US011484647B2

(12) United States Patent
Sakai et al.

(10) Patent No.: US 11,484,647 B2
(45) Date of Patent: Nov. 1, 2022

(54) MEDICINAL LIQUID INJECTION PORT AND MEDICINAL LIQUID INJECTION DEVICE

(71) Applicant: PIOLAX MEDICAL DEVICES, INC., Kanagawa (JP)

(72) Inventors: Shinichi Sakai, Kanagawa (JP); Yuuki Inami, Kanagawa (JP)

(73) Assignee: PIOLAX MEDICAL DEVICES, INC., Kanagawa (JP)

( * ) Notice: Subject to any disclaimer, the term of this patent is extended or adjusted under 35 U.S.C. 154(b) by 272 days.

(21) Appl. No.: 16/617,213

(22) PCT Filed: May 25, 2018

(86) PCT No.: PCT/JP2018/020195
§ 371 (c)(1),
(2) Date: Nov. 26, 2019

(87) PCT Pub. No.: WO2018/221417
PCT Pub. Date: Dec. 6, 2018

(65) Prior Publication Data
US 2020/0297926 A1 Sep. 24, 2020

(30) Foreign Application Priority Data

May 31, 2017 (JP) .............................. JP2017-108351

(51) Int. Cl.
*A61M 5/162* (2006.01)
*A61M 5/36* (2006.01)
(Continued)

(52) U.S. Cl.
CPC .............. *A61M 5/162* (2013.01); *A61M 5/36* (2013.01); *A61M 39/0208* (2013.01);
(Continued)

(58) Field of Classification Search
CPC ........ A61M 37/00; A61M 5/162; A61M 5/36; A61M 39/10; A61M 2039/0081;
(Continued)

(56) References Cited

U.S. PATENT DOCUMENTS 5,383,466 A * 1/1995 Partika ................. A61B 8/0833
600/459
2006/0264898 A1* 11/2006 Beasley ............ A61M 39/0208
428/36.9
(Continued)

FOREIGN PATENT DOCUMENTS

JP 3049179 U 6/1998
JP 2010-011914 A 1/2010
(Continued)

OTHER PUBLICATIONS

Jul. 10, 2018, International Search Report issued for related PCT Application No. PCT/JP2018/020195.
(Continued)

*Primary Examiner* — Lauren P Farrar
*Assistant Examiner* — Hamza A Darb
(74) *Attorney, Agent, or Firm* — Paratus Law Group, PLLC

(57) ABSTRACT

There is provided a medicinal liquid injection port to be implanted subcutaneously. A housing main body is provided with a medicinal liquid storage portion therein, an opening portion that opens the medicinal liquid storage portion, and a discharge hole that communicates with the medicinal liquid storage portion and configured to be connected with a tube. A septum attached to the opening portion of the housing main body and provided with a puncturable region that can be punctured with a puncture needle. A contrast portion is disposed in the septum over a thickness direction of the septum so as to detect the puncturable region of the septum with the ultrasonic wave. The contrast portion is provided in the septum within a thickness region of the septum and all of the contrast portion is positioned at an inner side of the septum in the thickness direction of the septum.

14 Claims, 5 Drawing Sheets

(51) Int. Cl.
  *A61M 39/02* (2006.01)
  *A61M 39/10* (2006.01)
  *A61M 39/00* (2006.01)
(52) U.S. Cl.
  CPC ..... *A61M 39/10* (2013.01); *A61M 2039/0081* (2013.01); *A61M 2039/0232* (2013.01)
(58) Field of Classification Search
  CPC .. A61M 2205/3693; A61M 2039/0232; A61M 2039/0238; A61M 39/0208
  See application file for complete search history.

(56) References Cited

U.S. PATENT DOCUMENTS

| | | | |
|---|---|---|---|
| 2011/0275930 A1 | 11/2011 | Jho et al. | |
| 2014/0276473 A1* | 9/2014 | Beling | B29C 37/0025 604/288.02 |
| 2018/0154075 A1 | 6/2018 | Jho et al. | |

FOREIGN PATENT DOCUMENTS

| | | |
|---|---|---|
| JP | 2012-200454 A | 10/2012 |
| JP | 2013-531999 A | 8/2013 |
| JP | 2016-064238 A | 4/2016 |
| JP | 2017-000496 A | 1/2017 |
| WO | WO 2007/122908 A1 | 11/2007 |

OTHER PUBLICATIONS

Jul. 10, 2018, International Search Opinion issued for related PCT Application No. PCT/JP2018/020195.
Jun. 4, 2019, PCT/IPEA/408 issued for related PCT Application No. PCT/JP2018/020195.
Sep. 27, 2019, PCT/IPEA/409 issued for related PCT Application No. PCT/JP2018/020195.
English-language translation of PCT/IPEA/409 issued for related PCT Application No. PCT/JP2018/020195.

* cited by examiner

MEDICINAL LIQUID INJECTION PORT AND MEDICINAL LIQUID INJECTION DEVICE

CROSS REFERENCE TO PRIOR APPLICATION

This application is a National Stage Patent Application of PCT International Patent Application No. PCT/JP2018/020195 (filed on May 25, 2018) under 35 U.S.C. § 371, which claims priority to Japanese Patent Application No. 2017-108351 (filed on May 31, 2017), which are all hereby incorporated by reference in their entirety.

TECHNICAL FIELD

The present invention relates to a medicinal liquid injection port configured to be implanted subcutaneously, into which medicinal liquid can be injected by puncturing with a puncture needle from the outside and a medicinal liquid injection device.

BACKGROUND ART

Conventionally, a medicinal liquid injection port is implanted subcutaneously as an instrument for efficiently injecting medicinal liquid such as an anti-cancer agent. In general, the medicinal liquid injection port includes a liquid reservoir portion therein, and an opening thereof is closed by a septum made of an elastic material. The medicinal liquid injection port is connected with a tube which is to be placed in a blood vessel such as the heart. When puncturing the septum with a puncture needle such as a non-coring needle from outside the body, and injecting medicinal liquid such as an anti-cancer agent, the medicinal liquid flows in the tube through the liquid reservoir portion, and the medicinal liquid is supplied to the blood vessel or the like.

However, since the septum of the medicinal liquid injection port cannot be visually recognized from outside the body, it is difficult to appropriately puncture the septum of the medicinal liquid injection port with the puncture needle. If the medicinal liquid is injected in a state in which the puncture needle has not been inserted into the septum, the medicinal liquid leaked out of the port causes inflammation in a tissue and necrosis of the tissue. In addition, although the medicinal liquid injection port should be implanted with the septum facing toward skin, in a case in which the medicinal liquid injection port is inverted and the liquid reservoir portion is positioned close to the skin, it is difficult to puncture the septum with the puncture needle.

Accordingly, it is desired that a position of the septum of the medicinal liquid injection port can be confirmed to be at an appropriate position. An X-ray marker for determining the position of the septum is provided at the medicinal liquid injection port, and the position of the septum can be grasped by X-ray contrast with CT. However, in this case, since the position of the septum can be grasped only in a dedicated diagnostic room having a CT facility, it is inconvenient. Therefore, a method has been developed that can grasp the position of the septum by a compact ultrasonic irradiation device that can be used in a hospital room, instead of CT.

For example, the following Patent Document 1 describes an access port having a marker that can be contrasted with ultrasonic irradiation, and the access port has a structure in which three markers are arranged on an outer periphery of a partition wall (a septum) of a main body so as to form a substantially triangular shape.

PRIOR ART DOCUMENT

Patent Document

Patent Document 1: Japanese Patent Application Publication No. 2016-64238 A

SUMMARY OF INVENTION

Problems to be Solved by Invention

In the access port of Patent Document 1 described above, when the access port is irradiated with an ultrasonic wave, a position of the septum can be grasped by the three markers on the outer periphery of the septum. However, since a surface of the septum is only partially contrasted on an echo image, it may be difficult to confirm the position of the septum.

An object of the present invention is to provide a medicinal liquid injection port and a medicinal liquid injection device for easily grasping a position of a septum under the skin by ultrasonic irradiation to appropriately puncture the septum with the puncture needle.

Means for Solving Problems

In order to achieve the above object, according to the present invention, there is provided a medicinal liquid injection port configured to be implanted subcutaneously, the medicinal liquid injection port into which medicinal liquid can be injected by puncturing with puncture needle from the outside, the medicinal liquid injection port including: a housing main body provided with a medicinal liquid storage portion therein, an opening portion that opens the medicinal liquid storage portion, and a discharge hole that communicates with the medicinal liquid storage portion and configured to be connected to a tube; and a septum attached to the opening portion of the housing main body and provided with a puncturable region that can be punctured with the puncture needle, wherein a contrast portion is disposed in the housing main body and/or the septum over a thickness direction of the septum so as to detect the puncturable region of the septum with the ultrasonic wave.

Advantageous Effects of Invention

According to the present invention, since the contrast portion is disposed in the housing main body and/or the septum over the thickness direction of the septum so as to detect the puncturable region of the septum, when the medicinal liquid injection port is irradiated with the ultrasonic wave, an echo image of the contrast portion is contrasted over the thickness direction of the septum so as to easily grasp a position of the puncturable region of the septum, so that the puncturable region of the septum can be appropriately punctured with the puncture needle.

EMBODIMENTS OF INVENTION

Hereinafter, an embodiment of a medicinal liquid injection port and a medicinal liquid injection device according to the present invention will be described with reference to the drawings.

Figure 1:
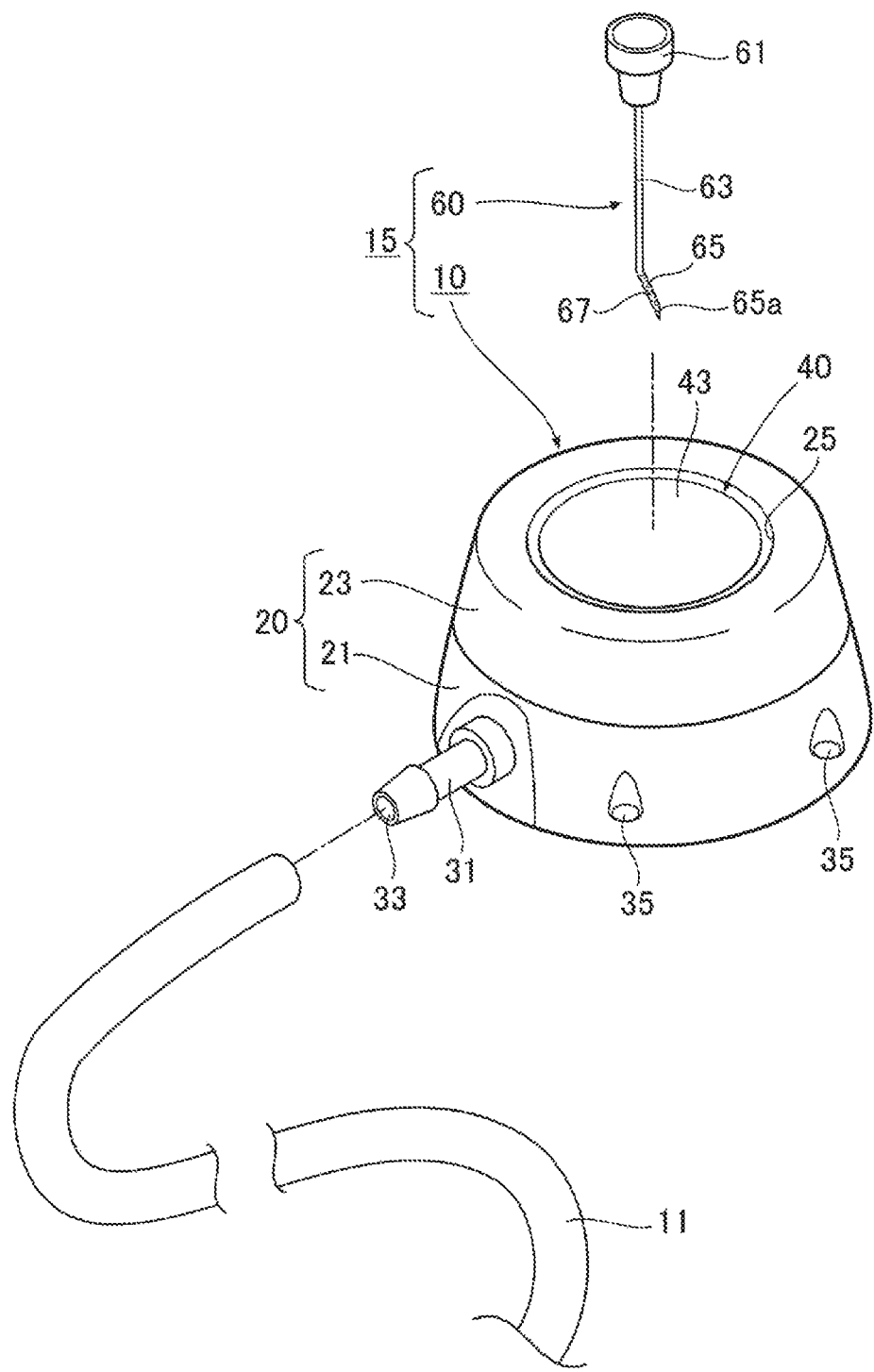
FIG. 1 is an exploded perspective view showing a medicinal liquid injection port and a medicinal liquid injection device according to an embodiment of the present invention.
Figure 3:
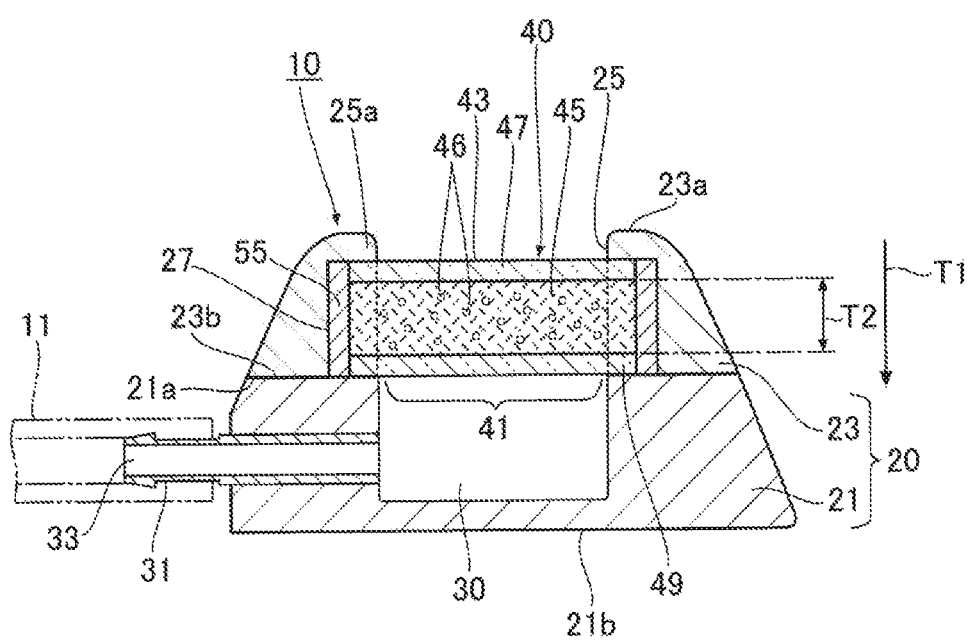
FIG. 3 is a sectional view of the medicinal liquid injection port.

As shown in FIGS. 1 and 3, a medicinal liquid injection port 10 (hereinafter, also simply referred to as "port 10") in this embodiment can be implanted subcutaneously to inject medicinal liquid by puncturing it with a puncture needle 60 from the outside. The medicinal liquid injection port 10 includes a housing main body 20 provided with a medicinal liquid storage portion 30 therein and an opening portion 25 that opens the medicinal liquid storage portion 30, and a septum 40 that is attached to the opening portion 25 of the housing main body 20.

In this embodiment, the housing main body 20 is formed of two parts of a base portion 21 and a lid portion 23, and a bottom surface 23b of the lid portion 23 is joined to a ceiling surface 21a of the base portion 21 by welding, adhesion, or the like to form a structure in which both parts are integrated. In addition, an outer peripheral surface of the housing main body 20 has a tapered shape gradually increasing in a diameter from a ceiling surface 23a (a surface opposite to the bottom surface 23b) of the lid portion 23 toward a bottom surface 21b (a surface opposite to the ceiling surface 21a) of the base portion 21, and has a substantially truncated cone shape as a whole.

The opening portion 25 having a circular shape is formed on the ceiling surface 23a side (a side opposite to a joining surface with the base portion 21) of the lid portion 23. As shown in FIG. 3, inside the lid portion 23, a septum attachment space 27 for disposing the septum 40 and attaching it to the opening portion 25 is formed in communication with the opening portion 25 at a deep side in a thickness direction (bottom surface 23b side) from the opening portion 25. The septum attachment space 27 has a shape whose diameter is larger than that of the opening portion 25, so that a peripheral edge portion 25a of the opening portion 25 has a thin flange shape. The peripheral edge portion 25a is locked to a ceiling surface side peripheral edge of the septum 40 disposed in the septum attachment space 27 to prevent the septum 40 from coming off from the opening portion 25. In addition, the peripheral edge portion 25a of the opening portion 25 extends in a flange shape so as not to overlap a contrast portion 45, which will be described later, of the septum 40. However, the peripheral edge portion 25a of the opening portion 25 may be shaped so as to be locked to a frame-shaped body 55, which will be described later, disposed on an outer periphery of the septum, and preferably the peripheral edge portion 25a has a shape that does not overlap the contrast portion 45 of the septum 40.

On the other hand, the medicinal liquid storage portion 30 is formed inside the base portion 21. The medicinal liquid storage portion 30 in this embodiment is opened at the top and has a circular concave shape with a diameter smaller than that of the septum attachment space 27 (see FIG. 3). Further, the medicinal liquid storage portion 30 is opened to the outside of the port through the septum attachment space 27 and the opening portion 25. In addition, an upper opening of the medicinal liquid storage portion 30 is closed by the septum 40 which is disposed in the septum attachment space 27 of the lid portion 23, and sealed so as not to leak out.

Figure 2:
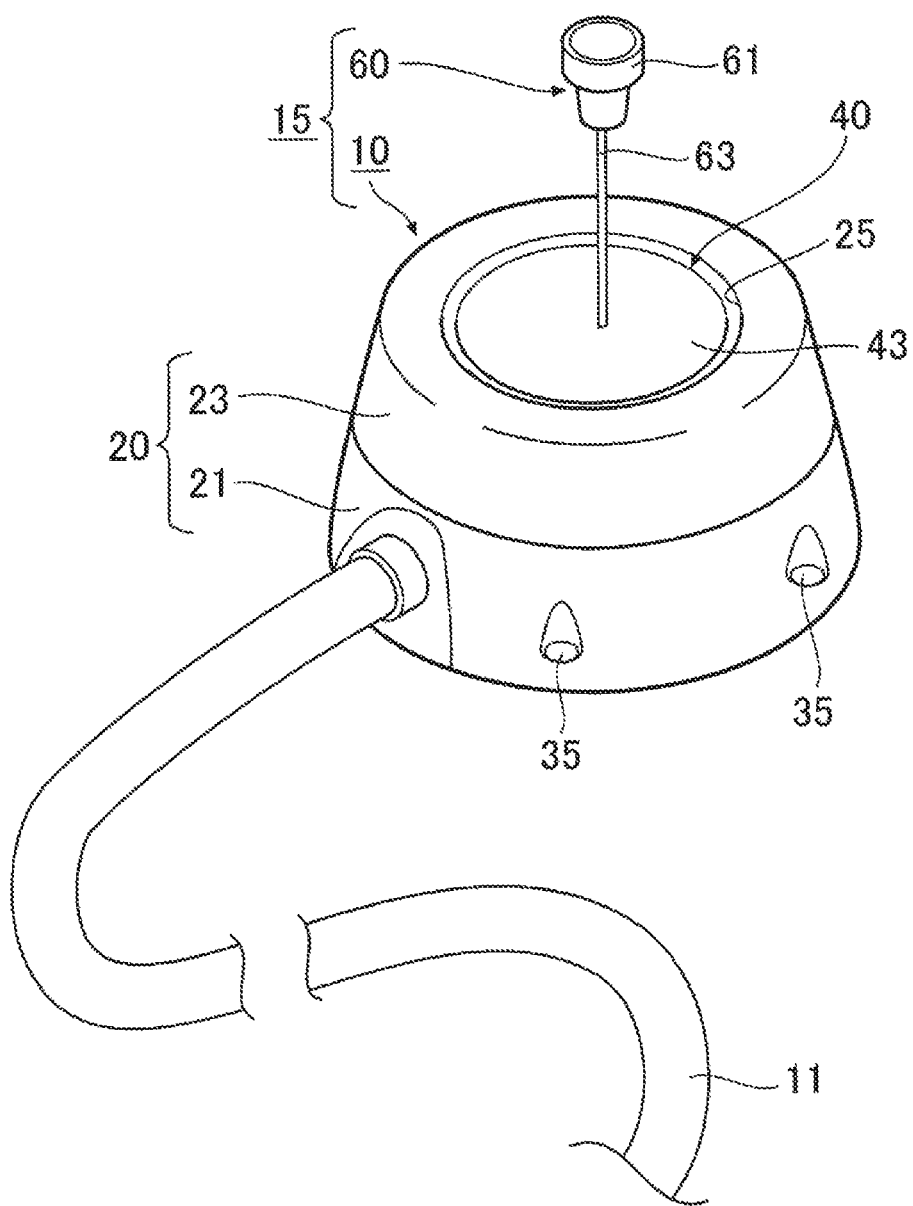
FIG. 2 is a perspective view of the medicinal liquid injection port and the medicinal liquid injection device.

As shown in FIG. 1, a connector 31 for connecting the tube 11 thereto is attached to the base portion 21. As shown in FIG. 3, an opening at a base end side of the connector 31 communicates with the medicinal liquid storage portion 30, and the connector 31 extends from an outer periphery of the base portion 21 in an outer diameter direction so as to connect the tube 11 to an outer periphery of a tip end side thereof. An opening on the tip end side of the connector 31 forms a discharge hole 33 through which the medicinal liquid stored in the medicinal liquid storage portion 30 is discharged to the tube 11. In addition, as shown in FIGS. 1 and 2, a plurality of holes 35 are formed at predetermined intervals on the outer periphery of the base portion 21 at a bottom surface side. A suture thread (not shown) can be inserted through the holes 35, and the suture thread is sewn to a predetermined site in the body to prevent displacement of the medicinal liquid injection port 10 implanted subcutaneously.

A shape and an internal structure of the housing main body 20 are merely examples. For example, the housing main body may not have a structure formed of two parts, and an outer periphery of the housing main body may have an elliptical shape or the like. The housing main body is not limited to the above shape and structure. In addition, the housing main body 20 may be formed of, for example, synthetic resin having biocompatibility such as nylon, polyethylene, polypropylene, fluororesin, polyimide, polyether sulfone resin, epoxy resin, polysulfone, polyacetal, liquid crystal polymer, polyurethane, silicone rubber, vinyl chloride resin, and polyethylene terephthalate resin, a metal having the biocompatibility such as Ti, stainless steel, or Ni—Ti alloy, a composite thereof, or the like. The connector 31 may be formed of, for example, a metal having the biocompatibility such as Ti, stainless steel, or Ni—Ti alloy, ceramic, hard resin, or super engineering plastic such as PEEK, a composite thereof, or the like.

On the other hand, the septum 40 has a disk shape that is larger than an inner diameter of the medicinal liquid storage portion 30 and has a predetermined thickness, and the frame-shaped body 55 having an annular shape is disposed on the outer periphery thereof (see FIG. 3). The frame-shaped body 55 prevents the septum 40 from coming out of the opening portion 25 of the housing main body 20 or reinforces the septum 40, but the frame-shaped body 55 may not be disposed.

The septum 40 is disposed in the septum attachment space 27 of the lid portion 23 together with the frame-shaped body 55 on the outer periphery thereof. In this state, the bottom surface 23b of the lid portion 23 is joined to the ceiling surface 21a of the base portion 21, so that the septum 40 is sandwiched between the peripheral edge portion 25a of the opening portion 25 and the ceiling surface 21a of the base portion 21, and the septum 40 is attached to the opening portion 25.

Figure 4:
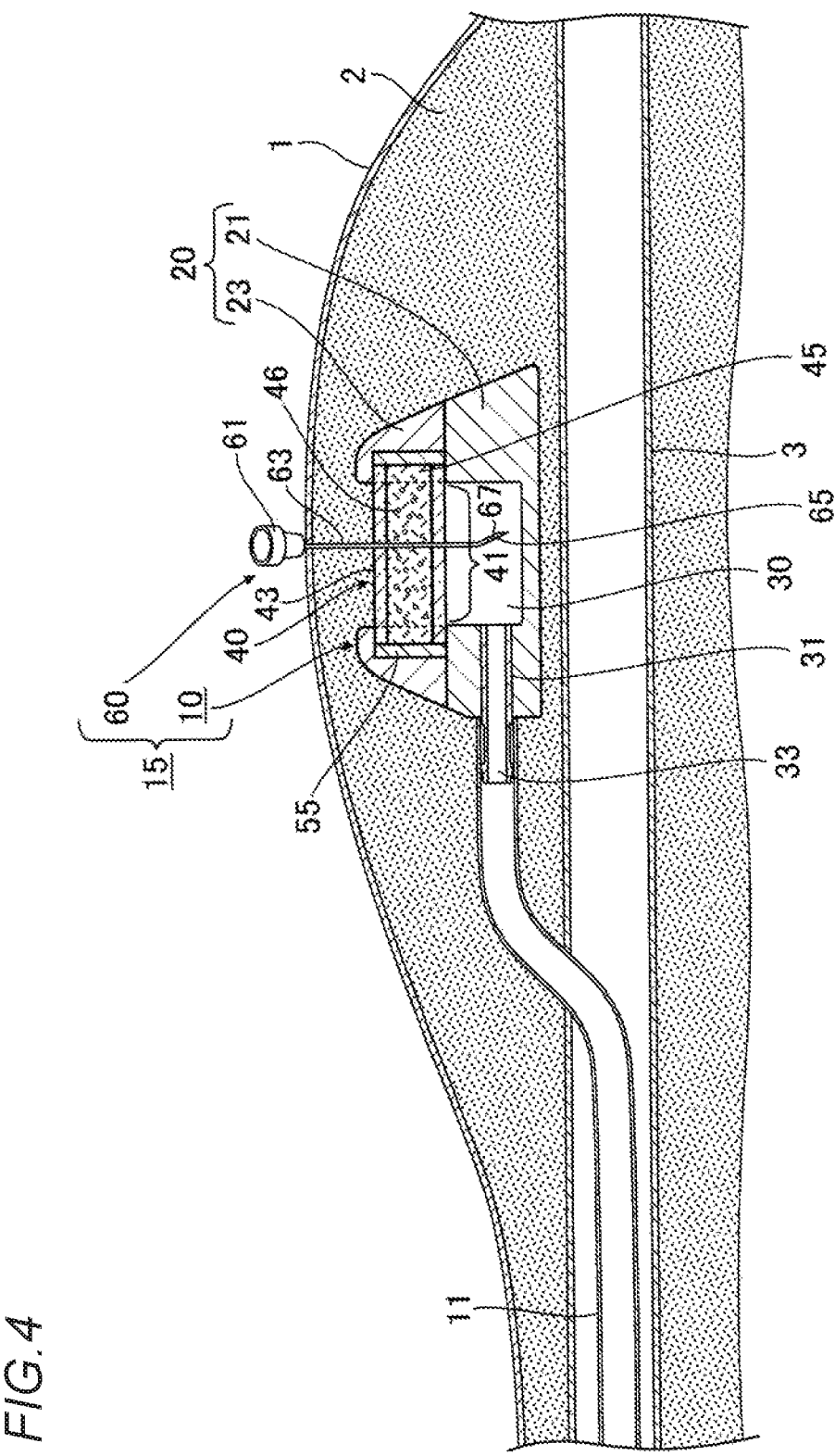
FIG. 4 is an explanatory diagram showing a use state of the medicinal liquid injection port and the medicinal liquid injection device.

As shown in FIGS. 3 and 4, the septum 40 is provided with a puncturable region 41 which can be punctured by the puncture needle 60. The puncturable region 41 means a region which can allow the puncture needle 60 to pass through the septum 40 up to the medicinal liquid storage portion 30 when puncturing it with the puncture needle 60 from a surface 43 (hereinafter, also simply referred to as an "exposed surface 43") of the septum 40, exposed through the opening portion 25. Herein, the puncturable region 41 is a region surrounded by left and right dashed lines on paper surfaces of FIGS. 3 and 4, and the puncturable region 41 excludes a region in which the puncture needle 60 hits the frame-shaped body 55 or the like when puncturing the septum 40 with the puncture needle 60 and the puncture needle 60 cannot reach the medicinal liquid storage portion 30. That is, the puncturable region 41 is a region that is disposed at a position aligned with the medicinal liquid storage portion 30 in the thickness direction of the port 10, and is in a range equal to or smaller than the inner diameter of the medicinal liquid storage portion 30.

The contrast portion 45 is disposed in the septum 40 over a thickness direction T1 of the septum 40 so as to detect the puncturable region 41 of the septum 40. Although the contrast portion 45 is disposed in the septum 40 in this embodiment, the contrast portion 45 may be disposed in the housing main body-side, and the contrast portion may also be disposed in both the housing main body and the septum.

The septum 40 in this embodiment includes the thick disk-shaped contrast portion 45 formed to have a predetermined thickness along the thickness direction T1, a thin disc-shaped exposed portion 47 disposed at a front side (one end surface side) of the contrast portion 45, and a thin disc-shaped bottom portion 49 disposed at a back side (the other end surface side) of the contrast portion 45. That is, the septum 40 has a three-layer structure in which the contrast portion 45 is disposed at a central portion in the thickness direction thereof, the exposed portion 47 is disposed at the front side of the contrast portion 45, and the bottom portion 49 is disposed at the back side of the contrast portion 45.

The exposed portion 47 of the septum 40 is disposed at a side of the opening portion 25 of the housing main body 20, and a surface thereof forms the exposed surface 43. Further, the bottom portion 49 closes the upper opening of the medicinal liquid storage portion 30.

In this embodiment, the septum 40 has a structure in which the contrast portion 45 is provided in a part of the septum 40 itself. Further, the contrast portion 45 in this embodiment is formed over the entire region in a radial direction of the septum 40 with an outer diameter larger than the inner diameter of the medicinal liquid storage portion 30, so as to cover the entire region of the medicinal liquid storage portion 30 in the radial direction thereof. In this embodiment, the contrast portion 45, the exposed portion 47, and the bottom portion 49 have the same outer diameter. The contrast portion, the exposed portion, and the bottom portion may have different outer diameters, and the outer diameters thereof are not particularly limited. In addition, although the exposed surface 43 of the septum 40 in this embodiment is positioned below an upper end position of the opening portion 25 of the housing main body 20, the exposed surface 43 of the septum 40 may be protruded so as to be positioned above an upper end of the opening portion 25 of the housing main body 20.

In this embodiment, by irradiating the medicinal liquid injection port 10 with the ultrasonic wave, the contrast portion 45 is contrasted in an echo image, so that the puncturable region 41 of the septum 40 can be detected over the thickness direction T1 of the septum 40.

The contrast portion only needs to be able to detect the puncturable region of the septum with the ultrasonic wave over the thickness direction of the septum, and location, shape, or the like of the contrast portion are not particularly limited. For example, the contrast portion may be formed in an outer peripheral portion of the septum over the thickness direction, and the contrast portion may be formed only in the puncturable region 41 without being formed over the entire region of the septum in the radial direction thereof.

The thickness direction T1 of the septum 40 means a direction orthogonal to the exposed surface 43 of the septum 40 (a direction perpendicular to a surface direction of the exposed surface 43), which is exposed through the opening portion 25 of the housing main body 20.

As the septum 40, a resin material is used, having elasticity that can be punctured with the puncture needle 60 and can self-seal (tack) a puncture hole formed by the puncture needle 60 when the puncture needle 60 is pulled out. Examples of such a resin material include silicone rubber, latex, fluororubber, isoprene, and styrene-based elastomer, for example.

As shown in FIG. 3, the contrast portion 45 in this embodiment is formed of a member containing air bubbles 46. In this embodiment, the air bubbles 46 are not contained in an outer periphery of the contrast portion 45 so as not to overlap the peripheral edge portion 25a of the opening portion 25 of the housing main body 20. However, the air bubbles 46 may also be contained in the outer periphery of the contrast portion 45 (this structure will be described in an embodiment described later). In addition, the air bubbles 46 can be contained, for example, by injection molding a resin material containing gas into a mold frame or injecting the gas into molten resin injected into the mold frame.

In the above embodiment, the air bubbles are contained in the contrast portion. However, except for containing the air bubbles, the following methods can be used to form the contrast portion. For example, (1) the contrast portion includes a resin, metal, or the like having a different acoustic impedance from that of a living body, (2) the contrast portion is provided with a layer of air instead of the air bubbles, (3) a front surface of the septum is uneven or roughened (in this case, the front surface of the septum having the uneven or the roughened surface forms the "contrast portion"), (4) the front surface of the septum is coated with a material having different acoustic impedance (in this case, the coating layer forms the "contrast portion").

As in the present embodiment, in a case of forming the septum 40 having a three-layer structure, for example, a resin material containing the gas and a resin material containing no gas are simultaneously injection-molded in a mold frame to form the contrast portion 45, the exposed portion 47, the bottom portion 49, or by injecting the resin material containing the gas into the mold frame and supercooling a part of the material in contact with an inner surface of the mold frame, the air bubbles 46 can be provided only in an inner side part (i.e., the contrast portion 45) which is not in contact with the inner surface of the mold frame without providing the air bubbles 46 in the part (that is, the exposed portion 47 and the bottom portion 49) in contact with the inner surface of the mold frame.

On the other hand, a medicinal liquid injection device 15 in this embodiment includes the port 10 having the above described structure and the puncture needle 60.

As shown in FIG. 1, the puncture needle 60 in this embodiment includes a connection portion 61 to which a syringe of an injector or a tip end portion of a drip (not shown) is detachably connected, a tubular straight line portion 63 that extends linearly from the connection portion 61, and a tip end portion 65 that has a tubular shape bent at a predetermined angle with respect to the straight line portion 63, and has a sharp blade tip.

A blade surface 65a of the tip end portion 65 is parallel to an axial direction of the straight line portion 63. That is, the puncture needle 60 is a well-known non-coring needle that does not scrape away a body of the septum 40 at the time of puncturing the septum 40. Further, the tip end portion 65 of the puncture needle 60 is provided with a detectable portion 67 that can be detected with the ultrasonic wave. The detectable portion 67 can be formed, for example, by performing a surface processing that makes the surface rougher than the straight line portion 63.

As shown in FIG. 4, the medicinal liquid injection device 15 is configured such that the detectable portion 67 is positioned in the medicinal liquid storage portion 30 of the housing main body 20 in a state in which the puncturable region 41 of the septum 40 is punctured with the puncture needle 60.

Next, operation and effect of the medicinal liquid injection port 10 and the medicinal liquid injection device 15 having the above described configuration will be described.

FIG. 4 shows a state in which the medicinal liquid injection device 15 is used with the port 10 implanted subcutaneously. That is, the port 10 is implanted so as to be embedded in a subcutaneous tissue 2 at an inner surface side of a skin 1 and the port 10 is able to supply a medicinal liquid such as an anti-cancer agent or a nutrient to a tubular organ 3 such as a blood vessel through the tube 11 connected to the connector 31 of the port 10.

When the port 10 is implanted subcutaneously, a tip end portion of the tube 11 is placed in a predetermined position of the tubular organ 3 by a well-known Seldinger method or the like, and then the base end portion of the tube 11 is connected to the connector 31 of the port 10 outside the body. The port 10 is disposed at a predetermined position of the subcutaneous tissue 2 by incising the skin 1, and the suture thread inserted into the plurality of holes 35 on the outer periphery of the port is sewn to a predetermined site, so that the port 10 is implanted to be embedded in the subcutaneous tissue 2. Thereafter, as shown in FIG. 4, by closing the incised skin 1, the port 10 can be placed subcutaneously (under the skin 1).

By irradiating the port 10 with the ultrasonic wave from an ultrasonic probe (probe) of an ultrasonic irradiation device (not shown), the echo image is contrasted on an monitor of the ultrasonic irradiation device.

At this time, in the port 10, since the septum 40 is provided with the contrast portion 45 over the thickness direction T1 of the septum 40 so that the puncturable region 41 of the septum 40 can be detected with the ultrasonic wave, when the port 10 is irradiated with the ultrasonic wave, the echo image of the contrast portion 45 is displayed on the monitor in a wide range over the thickness direction T1 of the septum 40, so that a position of the puncturable region 41 of the septum 40 can be grasped securely. As a result, a person who use the puncture needle 60 can smoothly puncture the puncturable region 41 of the septum 40 with the puncture needle 60.

Therefore, in the port 10, it is possible to easily grasp a position of the septum 40, particularly in the thickness direction T1 of the septum 40, under the skin at the time of the ultrasonic irradiation, and the septum 40 can be appropriately punctured so that the puncture needle 60 can appropriately puncture the septum 40 to reach the medicinal liquid storage portion 30. In addition, the puncture needle 60 can be prevented from being incorrectly inserted in a location other than the septum 40, and inflammation and necrosis of the tissue can be suppressed. If the septum 40 is not disposed at a position close to the skin 1 and is disposed in an inverted manner, it is easy to grasp that the septum 40 is disposed at a position far from the skin 1, and a subsequent treatment (the skin 1 is re-incised to correct an orientation of the septum 40, or the like) can be performed quickly, so that a burden on a patient can be suppressed.

As shown in FIG. 3, in this embodiment, since the contrast portion 45 is formed of a member containing the air bubbles 46, and when the port 10 is irradiated with the ultrasonic wave, the ultrasonic wave is irregularly reflected by the air bubbles 46, the echo image can be more easily contrasted over the thickness direction of the septum 40, and thus it becomes more easy to puncture the puncturable region 41 of the septum 40 with the puncture needle 60, and to grasp the position of the septum 40 (particularly, the thickness direction T1 of the septum 40) under the skin at the time of the ultrasonic irradiation, and the septum 40 can be appropriately punctured with the puncture needle 60 so that the puncture needle 60 can reach the medicinal liquid storage portion 30.

As shown in FIG. 3, in this embodiment, since the air bubbles 46 are provided in the septum 40, that is, in the contrast portion 45, when puncture the puncturable region 41 of the septum 40 with the puncture needle 60, a state in which the septum 40 is recessed by puncture pressure can be confirmed, and a puncture state of the puncture needle 60 can be easily grasped. In addition, since the air bubbles 46 are provided in the septum 40, the location where the echo image is contrasted is punctured with the puncture needle 60, and thus the puncture needle 60 can be easily inserted into the puncturable region 41 sensuously, so that the puncture needle 60 can be prevented from incorrectly being inserted into a region other than the puncturable region 41 (if a location where the echo image is contrasted and the puncturable region 41 are misaligned, a puncture location is likely to be mistaken). Further, puncture resistance of the puncture needle 60 with respect to the puncturable region 41 of the septum 40 can be reduced by the air bubbles 46 provided in the septum 40, and the puncture needle 60 can be smoothly inserted into the puncturable region 41 of the septum 40.

In this embodiment, the air bubbles 46 are provided in the puncturable region 41 of the septum 40 except for a part of the septum 40 that is exposed through the opening portion 25 of the housing main body 20 (the exposed portion 47 including the exposed surface 43). Accordingly, durability of the part of the septum 40 exposed through the opening portion 25 of the housing main body 20 can be increased to prevent the medicinal liquid from leaking to the outside of the septum. Further, since there are no air bubbles 46 in the exposed portion, the front surface portion (exposed surface 43) of the septum 40 exposed through the opening portion 25 of the housing main body 20 can be smoothed (effect of claim 5). In a case where the air bubbles 46 are not provided on the surface of the septum 40 at a side of the medicinal liquid storage portion 30 (a bottom surface on an opposite side to the exposed surface 43), the surface of the septum 40 at the side of the medicinal liquid storage portion 30 can be smoothed to prevent the medicine from entering into the septum 40 and remaining inside the septum.

On the other hand, as shown in FIG. 4, the medicinal liquid injection device 15 according to the present invention is configured such that the detectable portion 67 which is detectable with the ultrasonic wave is positioned in the medicinal liquid storage portion 30 of the port 10 in a state in which the puncturable region 41 of the septum 40 of the port 10 is punctured with the puncture needle 60 provided with the detectable portion 67 at the tip end portion 65.

Therefore, by irradiating the port 10 and the puncture needle 60 with the ultrasonic wave, the detectable portion 67 of the puncture needle 60 can be detected in addition to the puncturable region 41 of the septum 40, so that a position of the puncture needle 60 can be reliably grasped, and the puncture needle 60 can be more easily inserted into the puncturable region 41 of the septum 40.

Figure 5A:
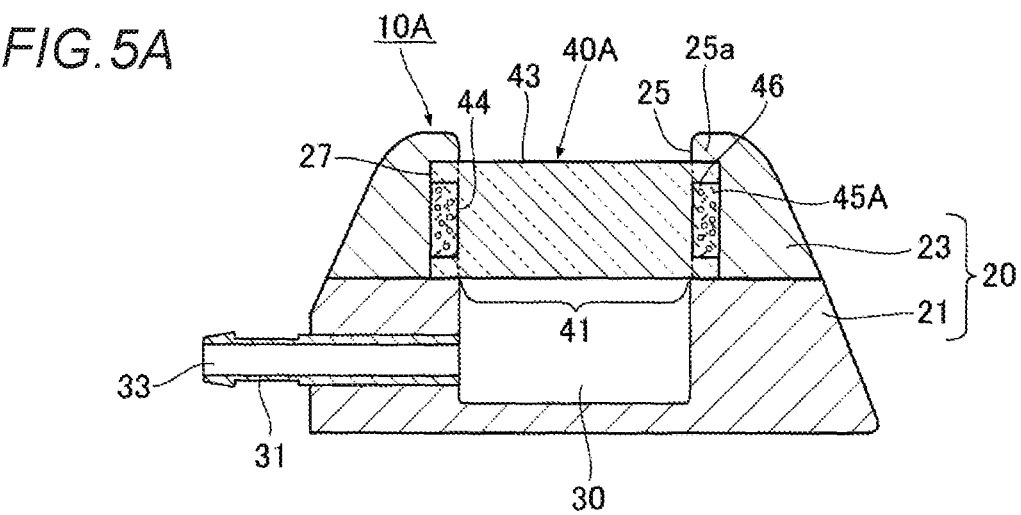
FIG. 5A is a sectional view showing a medicinal liquid injection port according to another embodiment of the present invention.

FIG. 5A shows a medicinal liquid injection port according to another embodiment of the present invention. Parts that are substantially the same as those of the above embodiment are given the same reference numerals, and descriptions thereof are omitted.

In a medicinal liquid injection port 10A (hereinafter, also simply referred to as "port 10A") in this embodiment, a contrast portion 45A provided with the air bubbles 46 is disposed on an outer periphery of the septum 40A. Specifically, a concave portion 44 having an annular shape is formed in the outer periphery of the septum 40A at a central portion in the thickness direction of the septum 40A, and the annular contrast portion 45A is fitted in the concave portion 44. That is, the air bubbles 46 are provided in the contrast portion 45A around the puncturable region 41 excluding the puncturable region 41 of the septum 40A.

The port 10A of this embodiment has the following operation and effect. The puncturable region 41 of the septum 40A is repeatedly punctured with the puncture needle 60, so that durability is reduced. However, according to the port 10A, since the air bubbles 46 are provided in the contrast portion 45A around the puncturable region 41 excluding the puncturable region 41 of the septum 40A, by contrasting a periphery of the puncturable region 41, the puncturable region 41 can be visually recognized while maintaining the durability of the puncturable region 41 of the septum 40A. In addition, since the air bubbles 46 are not provided in the puncturable region 41 of the septum 40A, a front surface part (exposed surface 43) of the septum 40A exposed through the opening portion 25 can be smoothed (effect of claim 4). In the case in which the air bubbles 46 are not provided on a surface of the septum 40A at the side of the medicinal liquid storage portion 30, the surface of the septum 40 at the side of the medicinal liquid storage portion 30 can be smoothed to prevent the medicine from entering into the septum 40A and remaining inside the septum.

Figure 5B:
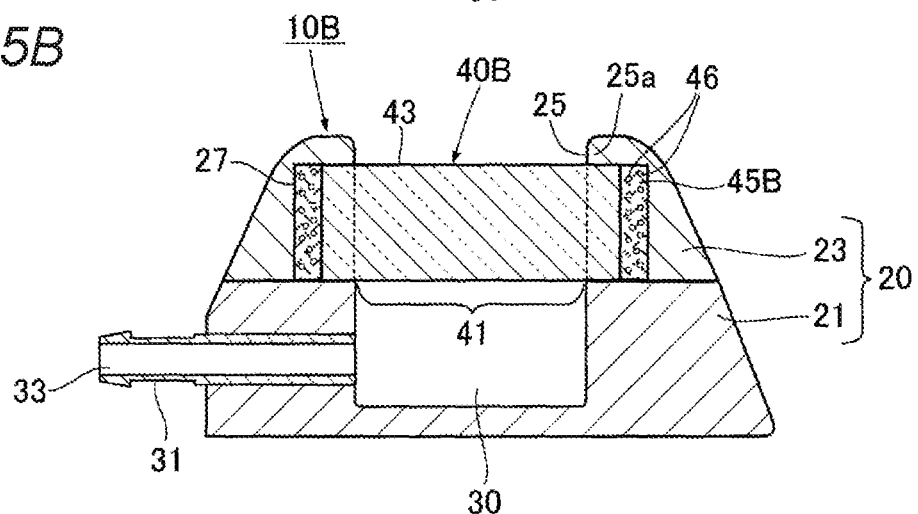
FIG. 5B is a sectional view showing a medicinal liquid injection port according to still another embodiment of the present invention.

FIG. 5B shows a medicinal liquid injection port according to still another embodiment of the present invention. Parts that are substantially the same as those of the above embodiment are given the same reference numerals, and descriptions thereof are omitted.

In a medicinal liquid injection port 10B (hereinafter, also simply referred to as "port 10B") in this embodiment, a contrast portion 45B provided with the air bubbles 46 is disposed in the housing main body 20. Specifically, the contrast portion 45B having an annular shape and containing the air bubbles 46 is disposed on an outer periphery of the septum 40B in the septum attachment space 27 of the housing main body 20. Similar to the port 10A of the above embodiment, the air bubbles 46 are provided in the contrast portion 45B around the puncturable region 41 excluding the puncturable region 41 of the septum 40B. Also in the port 10B of this embodiment, the same operation and effect as the port 10A of the above embodiment can be obtained.

Figure 5C:
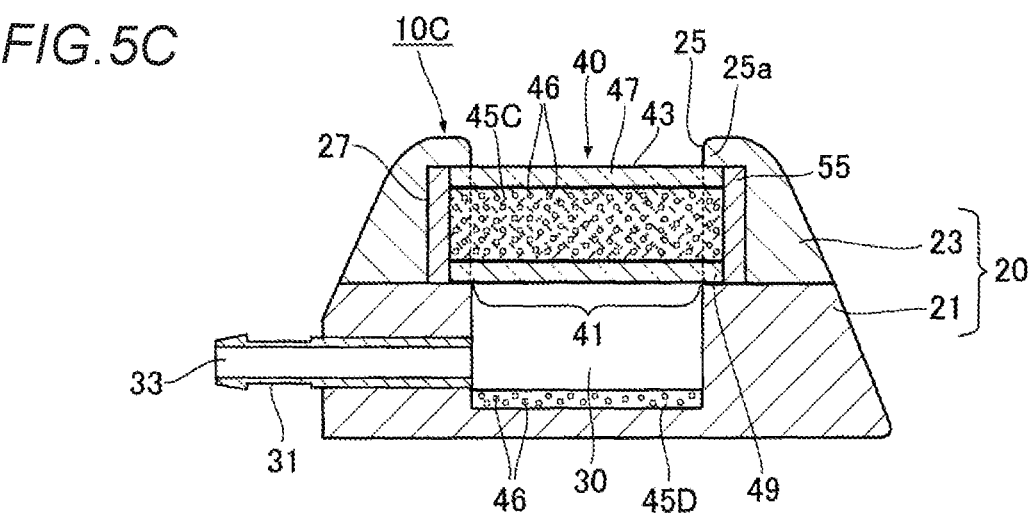
FIG. 5C is a sectional view showing a medicinal liquid injection port according to yet another embodiment of the present invention.

FIG. 5C shows a medicinal liquid injection port according to yet another embodiment of the present invention. Parts that are substantially the same as those of the above embodiment are given the same reference numerals, and descriptions thereof are omitted.

In the medicinal liquid injection port 10C (hereinafter, also simply referred to as "port 10C") in this embodiment, the septum 40 has a three-layer structure in which a contrast portion 45C is disposed at a central portion in the thickness direction, and the exposed portion 47 is disposed on the front side, and the bottom portion 49 is disposed on the back side, as in the embodiment shown in FIGS. 1 to 4. The contrast portion 45C has basically the same structure as that of the contrast portion 40 of the above embodiment, but the air bubbles 46 are also contained in the outer periphery thereof.

A contrast portion 45D having a disc shape and containing the air bubbles 46 is disposed at a bottom portion of the medicinal liquid storage portion 30.

The contrast portion 45D is disposed at a position that is aligned with the contrast portion 45C of the septum 40 in the thickness direction of the port 10C with a predetermined distance (depth of the medicinal liquid storage portion 30 excluding the contrast portion 45D) in the thickness direction of the port 10C. In addition, the contrast portion 45D is aligned with the puncturable region 41 of the septum 40) in the thickness direction of the port 10C.

In the port 10C of this embodiment, when irradiating with the ultrasonic wave, the contrast portion 45C provided in the septum 40 and the contrast portion 45D disposed at the bottom portion of the medicinal liquid storage portion 30 are contrasted at a predetermined distance, so that it is possible to firmly grasp a direction in which the puncture needle 60 should be inserted (that is, a direction toward a bottom portion side of the medicinal liquid storage portion 30), and it is possible to more accurately grasp whether or not the tip end of the puncture needle 60 reaches the medicinal liquid storage portion 30.

The present invention is not limited to the above-described embodiments, and various modified embodiments are possible within the scope of the present invention, and such embodiments are also included in the scope of the present invention.

DESCRIPTION OF REFERENCE NUMERALS 10, 10A, 10B, 10C Medicinal Liquid Injection Port (Port)
11 Tube
15 Medicinal Liquid Injection Device
20 Housing Main Body
25 Opening Portion
30 Medicinal Liquid Storage Portion
33 Discharge Hole
40, 40A, 40B Septum
41 Puncturable Region
45, 45A, 45B, 45C, 45D Contrast Portion
46 Air Bubble
60 Puncture Needle

The invention claimed is:

1. A medicinal liquid injection port configured to be implanted subcutaneously, the medicinal liquid injection port into which medicinal liquid can be injected by puncturing with a puncture needle from outside the medicinal liquid injection port, the medicinal liquid injection port comprising:
   a housing main body provided with a medicinal liquid storage portion therein, an opening portion that opens the medicinal liquid storage portion, and a discharge hole that communicates with the medicinal liquid storage portion and configured to be connected with a tube; and a septum attached to the opening portion of the housing main body and provided with a puncturable region that can be punctured with the puncture needle, wherein a contrast portion is disposed in the septum over a thickness direction of the septum so as to detect the puncturable region of the septum with an ultrasonic wave, wherein the contrast portion is provided in the septum within a thickness region of the septum and all of the contrast portion is positioned at an inner side of the septum in the thickness direction of the septum, wherein the septum is constituted by only three layers including: a layer including the contrast portion formed to have a predetermined thickness in the thickness direction; an exposed portion layer disposed at a front side of the contrast portion; and a bottom portion layer disposed at a back side of the contrast portion, wherein all of the contrast portion is positioned within the exposed portion layer and the bottom portion layer in a direction orthogonal to the thickness direction, wherein layer including the contrast portion is thicker than the exposed portion layer and the layer including the contrast portion is thicker than the bottom portion layer, and wherein the contrast portion is provided in an entire region of an exposed surface of the exposed portion layer in a radial direction of the exposed portion layer, the exposed surface being exposed from the opening portion of the housing main body.

2. The medicinal liquid injection port according to claim 1, wherein the contrast portion is formed of a member containing air bubbles.

3. The medicinal liquid injection port according to claim 1, wherein the contrast portion is formed of a member containing air bubbles and the air bubbles are provided in the contrast portion that is disposed in the septum.

4. The medicinal liquid injection port according to claim 1, wherein the contrast portion is formed of a member containing air bubbles and the air bubbles are provided in the puncturable region of the septum excluding a part of the septum, exposed from the opening portion.

5. A medicinal liquid injection device comprising:
the medicinal liquid injection port according to claim 1; and
a puncture needle provided with a detectable portion that is detectable with the ultrasonic wave at a tip end portion thereof,
wherein the detectable portion is configured to be positioned in the medicinal liquid storage portion of the housing main body in a state in which the puncturable region of the septum is punctured with the puncture needle.

6. A medicinal liquid injection port configured to be implanted subcutaneously, the medicinal liquid injection port into which medicinal liquid can be injected by puncturing with a puncture needle from outside the medicinal liquid injection port, the medicinal liquid injection port comprising:
a housing main body provided with a medicinal liquid storage portion therein, an opening portion that opens the medicinal liquid storage portion, and a discharge hole that communicates with the medicinal liquid storage portion and configured to be connected with a tube; and
a septum attached to the opening portion of the housing main body and provided with a puncturable region that can be punctured with the puncture needle, wherein a contrast portion is disposed in the septum over a thickness direction of the septum so as to detect the puncturable region of the septum with an ultrasonic wave, wherein the contrast portion is provided in the septum within a thickness region of the septum and all of the contrast portion is positioned at an inner side of the septum in the thickness direction of the septum, wherein a concave portion having an annular shape is formed in a side surface of an outer periphery of the septum at a central portion in the thickness direction of the septum, the side surface being in contact with the housing main body, the concave portion formed by cutting off the side surface, and the contrast portion having an annular shape is disposed in the concave portion, and wherein the contrast portion is provided around the puncturable region excluding the puncturable region of the septum, the contrast portion being positioned along an axis that is located within both the contrast portion and the puncturable region and is orthogonal to the thickness direction of the septum.

7. The medicinal liquid injection port according to claim 6, wherein the contrast portion is formed of a member containing air bubbles.

8. The medicinal liquid injection port according to claim 6, wherein the contrast portion is formed of a member containing air bubbles and the air bubbles are provided in the contrast portion that is disposed in the septum around the puncturable region excluding the puncturable region of the septum.

9. The medicinal liquid injection port according to claim 6, wherein the contrast portion is formed of a member containing air bubbles and the air bubbles are provided in the puncturable region of the septum excluding a part of the septum, exposed from the opening portion.

10. A medicinal liquid injection device comprising:
the medicinal liquid injection port according to claim 6; and
a puncture needle provided with a detectable portion that is detectable with the ultrasonic wave at a tip end portion thereof,
wherein the detectable portion is configured to be positioned in the medicinal liquid storage portion of the housing main body in a state in which the puncturable region of the septum is punctured with the puncture needle.

11. A medicinal liquid injection port configured to be implanted subcutaneously, the medicinal liquid injection port into which medicinal liquid can be injected by puncturing with a puncture needle from outside the medicinal liquid injection port, the medicinal liquid injection port comprising:
a housing main body provided with a medicinal liquid storage portion therein, an opening portion that opens the medicinal liquid storage portion, and a discharge hole that communicates with the medicinal liquid storage portion and configured to be connected with a tube; and
a septum attached to the opening portion of the housing main body and provided with a puncturable region that can be punctured with the puncture needle, wherein a contrast portion is disposed in the housing main body over a thickness direction of the septum so as to detect the puncturable region of the septum with an ultrasonic wave, wherein the contrast portion is provided in an outer periphery of the septum within a thickness region of the septum and all of the contrast portion is positioned at an inner side of the housing main body in a thickness direction of the housing main body, wherein the contrast portion is formed over an entire region in the thickness direction of the septum and disposed in an attachment space which is provided between the outer periphery of the septum and an inner periphery of the housing main body, wherein the contrast portion is in contact with the housing main body in a radial direction of the septum, and wherein the contrast portion is provided around the puncturable region excluding the puncturable region of the septum, the contrast portion being positioned along an axis that is located within both the contrast portion and the puncturable region and is orthogonal to the thickness direction of the septum.

12. The medicinal liquid injection port according to claim 11, wherein the contrast portion is formed of a member containing air bubbles.

13. The medicinal liquid injection port according to claim 11, wherein the contrast portion is formed of a member containing air bubbles and the air bubbles are provided in the contrast portion that is disposed in the septum around the puncturable region excluding the puncturable region of the septum.

14. A medicinal liquid injection device comprising:

the medicinal liquid injection port according to claim 11; and a puncture needle provided with a detectable portion that is detectable with the ultrasonic wave at a tip end portion thereof, wherein the detectable portion is configured to be positioned in the medicinal liquid storage portion of the housing main body in a state in which the puncturable region of the septum is punctured with the puncture needle.

* * * * *